(12) United States Patent
Sun et al.

(10) Patent No.: US 9,427,452 B2
(45) Date of Patent: Aug. 30, 2016

(54) METHOD FOR PREPARING FERMENTATION BROTH OF FRUITS AND VEGETABLES

(71) Applicant: Jilin Zixin Pharmaceutical Research Institution LLC., Changchun, Jilin (CN)

(72) Inventors: Dejun Sun, Jilin (CN); Jinlong Yin, Jilin (CN); Miaonan Sun, Jilin (CN); Yizhuo Zhao, Jilin (CN); Chunsheng Guo, Jilin (CN); Yanhui Gao, Jilin (CN); Xue Li, Jilin (CN)

(73) Assignee: Jilin Zixin Pharmaceutical Research Institution LLC., Changchun, Jilin (CN)

( * ) Notice: Subject to any disclaimer, the term of this patent is extended or adjusted under 35 U.S.C. 154(b) by 297 days.

(21) Appl. No.: 13/947,041

(22) Filed: Jul. 20, 2013

(65) Prior Publication Data

US 2013/0302454 A1    Nov. 14, 2013

Related U.S. Application Data

(63) Continuation-in-part of application No. PCT/CN2011/077173, filed on Jul. 14, 2011.

(30) Foreign Application Priority Data

Jan. 21, 2011    (CN) .......................... 2011 1 0023826

(51) Int. Cl.
| | | |
|---|---|---|
| C12P 1/04 | (2006.01) | |
| C12N 1/20 | (2006.01) | |
| A61K 35/74 | (2015.01) | |
| A23L 1/212 | (2006.01) | |
| A23L 1/30 | (2006.01) | |

(52) U.S. Cl.
CPC ............... *A61K 35/74* (2013.01); *A23L 1/212* (2013.01); *A23L 1/3002* (2013.01); *C12N 1/20* (2013.01); *C12P 1/04* (2013.01)

(58) Field of Classification Search
None
See application file for complete search history.

(56) References Cited

U.S. PATENT DOCUMENTS

| | | | | | |
|---|---|---|---|---|---|
| 5,639,648 | A | * | 6/1997 | Mainzer ............... | A23C 9/1238 435/207 |
| 5,676,985 | A | * | 10/1997 | Fletcher ............. | A23C 19/0323 426/34 |
| 2008/0175952 | A1 | * | 7/2008 | Terragno ............... | A23C 9/1234 426/20 |
| 2010/0034924 | A1 | * | 2/2010 | Fremaux ............... | A23C 9/1238 426/43 |
| 2010/0093617 | A1 | * | 4/2010 | Barrangou ........... | C12N 15/746 514/6.9 |

FOREIGN PATENT DOCUMENTS

| | | |
|---|---|---|
| CN | 102078354 | 6/2011 |
| CN | 102078354 A | 6/2011 |
| CN | 102078486 | 6/2011 |
| CN | 102078512 | 6/2011 |
| CN | 102078541 | 6/2011 |
| EP | 1169925 | 1/2002 |
| EP | 1169925 A1 | 1/2002 |

OTHER PUBLICATIONS

Anti-fatigue effect of Bifidobacterium-fermented mixed fruit and vegetable juice in mice.

* cited by examiner

*Primary Examiner* — Chris R Tate
*Assistant Examiner* — Douglas F White

(57) ABSTRACT

A method for preparing fermentation broth of fruits and vegetables includes steps of mixing fruits, vegetables, bacteria liquid of *Lactobacillus acidophilus*, bacteria liquid of *Bifidobactreium longum*, bacteria liquid of *Lactobacillus delbrueckii* subsp. *bulgaricus*, and bacteria liquid of *Streptococcus thermophilus*, and processing fermentation to obtain the fermentation broth of fruits and vegetables. A fermenting course of the method could be controlled, and a fermenting period is reduced to 15 days.

17 Claims, No Drawings

METHOD FOR PREPARING FERMENTATION BROTH OF FRUITS AND VEGETABLES

CROSS REFERENCE OF RELATED APPLICATION

This is a Continuation-In-Parts application of the International Application PCT/CN2011/077173, filed on Jul. 14, 2011, which claims the benefit of CN 201110023826.6 and priority date of Jan. 21, 2011.

BACKGROUND OF THE PRESENT INVENTION

1. Field of Invention

The present invention relates to a method for preparing fermentation broth of fruits and vegetables.

2. Description of Related Arts

It is shown in the prior researches that the enzyme of fruits and vegetables has following physiological functions of:

(1) clearing up the internal environment of human body, purifying blood, improving physique, decomposing and removing foreign matters, and preventing the chronic diseases and degenerative diseases;

(2) improving the carrying ability of the white blood cells, promoting the functions of the white blood cells, and improving anti-inflammatory ability, antibacterial ability, and self-healing ability of the body;

(3) taking part in digestion and decomposition of foods, and promoting recovery of body strength, wherein the multiple factors of the enzyme take part in digestion and decomposition of foods, in such a manner that foods are easier to be digested and decomposed;

(4) promoting the metabolism of cells, producing energy, and promoting regeneration of the cells in sub-health;

(5) reviving the reproductive cells which have decayed, and improving the reproductive function;

(6) alleviating the hangover, and preventing being drunk; and (7) supplementing nutrition and energy.

In a conventional method of preparing the enzyme, fruits and vegetables are smashed into pieces, and fermented with water under an anaerobic condition. In this fermentation, neither the fermenting course nor the strains of the bacteria taking parting in the fermentation could not be controlled, in such a manner that some bacteria may produce some substances harmful to human body, and the fermenting period is long (usually 3~6 months).

SUMMARY OF THE PRESENT INVENTION

An object of the present invention is to provide a method for preparing fermentation broth of fruits and vegetables.

The method provided by the present invention comprises following steps of:

mixing fruits, vegetables, bacteria liquid of *Lactobacillus acidophilus*, bacteria liquid of *Bifidobactreium longum*, bacteria liquid of *Lactobacillus delbrueckii* subsp. *bulgaricus*, and bacteria liquid of *Streptococcus thermophilus*, and processing fermentation to obtain a fermentation product, i.e. the fermentation broth of fruits and vegetables.

A fermentation temperature is 18° C.~37° C., wherein the fermentation temperature is preferably embodied as 18° C., 23° C., or 37° C. A fermenting period is 10 days~180 days, wherein the fermenting period is preferably embodied as 10 days, 15 days, or 180 days. A fermentation method comprises stirring while fermentation.

The method further comprises smashing the fruits and the vegetables into pieces of 40~50 meshes before the step of fermentation.

The method further comprises filtering the fermentation product after the step of fermentation, collecting filtrate, processing ultrafiltration, and collecting liquid produced by the ultrafiltration, i.e., the fermentation broth of fruits and vegetables.

The step of ultrafiltration comprises ultrafiltering the filtrate in a molecular weight of 100,000, wherein a liquid inlet pressure is 1.3 kg, and a liquid outlet pressure is 0.5 kg.

The fruits and the vegetables refer to a mixture of following 54 kinds of fruits and vegetables, which are konjak, eggplant, asparagus, spinach, bean sprout, broccoli, cabbage, radish, cucumber, peas, red pepper, celery, scallion, garlic, grapes, grapefruit, watermelon, peach, tangerine, blue berry, sweet orange, banana, litchi, balsam pear, leek, pomegranate, pitaya, carrot, tomato, Chinese cabbage, parsley, bell pepper, lettuce, pear, ginger, taro, kidney bean, pumpkin, lotus root, cherry, kiwi fruit, plum, strawberry, fig, kumquat, mandarin orange, Nanguo pear, cantaloup, Hami melon, papaya, onion, mulberry, sugar beet, and lemon.

Mass of each fruit or vegetable is equal with each other.

A proportion of the bacteria liquid of *Lactobacillus acidophilus*, the bacteria liquid of *Bifidobactreium longum*, the bacteria liquid of *Lactobacillus delbrueckii* subsp. *bulgaricus*, the bacteria liquid of *Streptococcus thermophilus*, the fruits and vegetables, and water is (2000~8000) ml:(2000~8000) ml:(2000~8000) ml:(2000~8000) ml:(1000~1500) kg:(1000~1500) kg.

The proportion of the bacteria liquid of *Lactobacillus acidophilus*, the bacteria liquid of *Bifidobactreium longum*, the bacteria liquid of *Lactobacillus delbrueckii* subsp. *bulgaricus*, the bacteria liquid of *Streptococcus thermophilus*, the fruits and vegetables, and water is preferably embodied as (2000, 5000, or 8000) ml:(2000, 5000, or 8000) ml:(2000, 5000, or 8000) ml:(2000, 5000, or 8000) ml:(1000, 1200, or 1500) kg:(1000, 1200, or 1500) kg.

The bacteria liquid of *Lactobacillus acidophilus* is prepared by a following method comprising: fermenting and cultivating *Lactobacillus acidophilus* to obtain a fermented product, i.e., the bacteria liquid of *Lactobacillus acidophilus*. A fermenting temperature is 20° C.~41° C., wherein the fermenting temperature is preferably embodied as 20° C., 37° C., or 41° C. A fermenting period is 15 h~36 h, wherein the fermenting period is preferably embodied as 15 h, 16 h, or 36 h.

The bacteria liquid of *Bifidobactreium longum* is prepared by a following method comprising: fermenting and cultivating *Bifidobactreium longum* to obtain a fermented product, i.e., the bacteria liquid of *Bifidobactreium longum*. A fermenting temperature is 20° C.~41° C., wherein the fermenting temperature is preferably embodied as 20° C., 37° C., or 41° C. A fermenting period is 15 h~36 h, wherein the fermenting period is preferably embodied as 15 h, 16 h, or 36 h.

The bacteria liquid of *Lactobacillus delbrueckii* subsp. *bulgaricus* is prepared by a following method comprising steps of: fermenting and cultivating *Lactobacillus delbrueckii* subsp. *bulgaricus* to obtain a fermented product, i.e. the bacteria liquid of *Lactobacillus delbrueckii* subsp. *bulgaricus*. A fermenting temperature is 20° C.~41° C., wherein the fermenting temperature is preferably embodied as 20°

C., 37° C., or 41° C. A fermenting period is 15 h~36 h, wherein the fermenting period is preferably embodied as 15 h, 16 h, or 36 h.

The bacteria liquid of *Streptococcus thermophilus* is prepared by a following method comprising steps of: fermenting and cultivating *Streptococcus thermophilus* to obtain a fermented product, i.e. the bacteria liquid of *Streptococcus thermophilus*. A fermenting temperature is 20° C.~41° C., wherein the fermenting temperature is preferably embodied as 20° C., 37° C., or 41° C. A fermenting period is 15 h~36 h, wherein the fermenting period is preferably embodied as 15 h, 16 h, or 36 h.

The *Lactobacillus acidophilus* is preferably embodied as *Lactobacillus acidophilus* CGMCC 1.1854, the *Bifidobactreium longum* is preferably embodied as *Bifidobactreium longum* CGMCC 1.2186, the *Lactobacillus delbrueckii* subsp. *bulgaricus* is preferably embodied as *Lactobacillus delbrueckii* subsp. *bulgaricus* CGMCC 1.1480, and the *Streptococcus thermophilus* is preferably embodied as *Streptococcus thermophilus* CGMCC 1.2471.

A medium of fermenting and cultivating is prepared by a method comprising: mixing 10 g of peptone, 10 g of beef extract, 5 g of yeast extract, 20 g of glucose, 1 g of tween-80, 2 g of $K_2HPO_4$, 1 g of tween-80, 5 g of NaAC, 2 g of ammonium citrate tribasic, 0.2 g of $MgSO_4$, 0.05 g of $MnSO_4$, and water, wherein a volume of the medium is up to 1 L by adding the water.

The fermentation broth of fruits and vegetables prepared by the above method is also in a protecting range of the present invention.

An applications of the above method or the fermentation broth of fruits and vegetables in a medicine for improving immunity, reducing fatigue, strengthening spleen and stomach, or removing chloasma is also in a protecting range of the present invention.

It is proved by experiments in the present invention that 4 kinds of probiotics comprising *Lactobacillus acidophilus*, *Bifidobactreium longum*, *Lactobacillus delbrueckii* subsp. *bulgaricus* and *Streptococcus thermophilus* are selected to take part in the fermentation, in such a manner that a fermenting course could be controlled, and a fermenting period is reduced to 15 days. Metabolites of the probiotics are benefit to human body. Enzyme of fruits and vegetables (the fermentation broth) in the present invention is a full-functional natural food produced by fermenting extracts of 80 kinds of natural vegetables and fruits and the probiotics. The fermentation broth contains full vitamins, mineral substances, and amino acids. The fermentation broth could provide complete nutrients to cells to repair the cells, and increase an efficiency of biochemical reactions, wherein the cells reacts to form other beneficial components.

The *Lactobacillus acidophilus*, the *Bifidobactreium longum*, the *Lactobacillus delbrueckii* subsp. *bulgaricus* and the *Streptococcus thermophilus* are all available on the China General Microbiological Culture Collection Center, CGMCC. http://www.cgmcc.net/

TABLE 1

*Lactobacillus acidophilus* CGMCC 1.1854

| | |
|---|---|
| No. | 1.1854 |
| Generic name | Lactobacillus |
| Specific epithet | Acidophilus |
| Isolation No. | ABT-A |
| History of culture | Microbiology Research Institute of China Science Academy |
| Biohazard | Fourth class |

TABLE 1-continued

*Lactobacillus acidophilus* CGMCC 1.1854

| | |
|---|---|
| Application | Fermentation of milk product, food and beverage |
| Culture temperature | 37° C. |
| Culture medium | 6 |
| Isolation source | Mixed milk starter cultures |
| Direct source | China |

See http://www.cgmcc.net/directory/detial.php?no=9592

TABLE 2

*Bifidobactreium longum* CGMCC 1.2186

| | |
|---|---|
| No | 1.2186 |
| Generic name | Bifidobacterium |
| Specific epithet | longum subsp. longum |
| Isolation No | JCM 1217 |
| History of culture | JCM |
| Biohazard | Fourth class |
| Application | Type strain |
| Culture temperature | 37° C. |
| Culture medium | 233 |
| Isolation source | Adult intestine |
| Direct source | Japan |

See http://www.cgmcc.net/directory/detial.php?no=8302

TABLE 3

*Lactobacillus delbrueckii* subsp. *bulgaricus* CGMCC 1.1480

| | |
|---|---|
| No | 1.1480 |
| Generic name | Lactobacillus |
| Specific epithet | delbrueckii subsp. bulgaricus |
| Isolation No. | 6-1 |
| History of culture | Microbiology Research Institute of China Science Academy |
| Biohazard | Fourth class |
| Application | Yoghurt |
| Culture temperature | 37° C. |
| Culture medium | 44 |
| Direct source | China |

See http://www.cgmcc.net/directory/detial.php?no=9643

TABLE 4

*Streptococcus thermophilus* CGMCC 1.2471

| | |
|---|---|
| No. | 1.2471 |
| Generic name | Streptococcus |
| Specific epithet | thermophilus |
| Isolation No. | 2000-8 |
| History of culture | Microbiology Research Institute of China Science Academy |
| Biohazard | Fourth class |
| Application | Probiotics |
| Culture temperature | 37° C. |
| Culture medium | 6 |
| Isolation source | Health care capsules |
| Original source | China |
| Direct source | China |

See http://www.cgmcc.net/directory/detial.php?no=11414.

These and other objectives, features, and advantages of the present invention will become apparent from the following detailed description, the accompanying drawings, and the appended claims.

DETAILED DESCRIPTION OF THE PREFERRED EMBODIMENT

Experimental methods used in following embodiments are all conventional method, if there is no special instruction.

Material, reagents, etc. used in the following embodiments could all be obtained by a commercial way, if there is no special instruction.

Example 1

Preparing Fermentation Broth of Fruits and Vegetables

Method 1

I. Fruits and Vegetables Selected 54 kinds of fruits and vegetables are listed as followed.

TABLE 1

| \multicolumn{4}{c}{Fruits and vegetables} | | | |
|---|---|---|---|
| Material | Nutritional ingredient | Material | Nutritional ingredient |
| Konjac | Vitamin B1, B2, citric acid, fermentation product | Carrot | Vitamin A, carotene, fermentation product |
| Eggplant | Vitamin A, B1, B2, C, fermentation product | Tomato | Vitamin A, carotene, citric acid, fermentation product |
| *Asparagus* | Vitamin B1, B2, citric acid, fermentation product | Chinese cabbage | Vitamins, mineral substances, fermentation product |
| Spinach | Vitamin A, C, ferrum, calcium, fermentation product | Parsley | Vitamins, mineral substances, fibers, fermentation product |
| Bean sprout | Vitamin, soap, amino acid, fermentation product | Bell pepper | Vitamin C, mineral substances, fermentation product |
| Broccoli | Vitamin B1, B2, citric acid, fermentation product | Lettuce | Vitamin A, mineral substances, fermentation product |
| Cabbage | Vitamin B1, B2, citric acid, fermentation product | Pear | Fructose, mineral substances, fermentation product |
| Radish | Vitamin B1, B2, citric acid, fermentation product | Ginger | Vitamins, mineral substances, fermentation product |
| Cucumber | Vitamin B1, B2, citric acid, fermentation product | Taro | Vitamin B1, B2, C, mineral substances, fermentation product |
| Pea | Vitamin B1, B2, citric acid, fermentation product | Kidney beans | Vitamin B1, B2, citric acid, fermentation product |
| Red pepper | Vitamin B1, B2, citric acid, fermentation product | Pumpkin | Carotene, mineral substances, fermentation product |
| Celery | Vitamin B1, B2, citric acid, fermentation product | Lotus root | Ferrum, tannin, fermentation product |
| Scallion | Vitamin B1, B2, citric acid, fermentation product | Cherry | mineral substances, fermentation product |
| Garlic | Vitamin B1, B2, citric acid, fermentation product | Kiwi fruit | Vitamin C, fermentation product |
| Grapes | Vitamin B1, B2, citric acid, fermentation product | Plum | organic acid, vitamins, fermentation product |
| Grapefruit | Vitamin B1, B2, citric acid, fermentation product | Strawberry | Vitamin C, mineral substances, ellagic acid, fermentation product |
| Watermelon | Vitamin B1, B2, citric acid, fermentation product | Fig | fermentation product, vitamins, mineral substances |
| Peach | Vitamin B1, B2, citric acid, fermentation product | Kumquat | Vitamin B1, B2, C, fermentation product |
| Tangerine | Vitamin B1, B2, C, fermentation product | Mandarin orange | Vitamin C, citric acid, fermentation product |
| Blueberry | Vitamin B1, B2, citric acid, fermentation product | Nanguo pear | Vitamin B1, B2, C, citric acid, fermentation product |
| Sweet orange | Vitamin B1, B2, citric acid, fermentation product | Cantaloup | Vitamin B1, B2, citric acid, fermentation product |
| Banana | Vitamin B1, B2, citric acid, fermentation product | Hami melon | Fructose, potassium, vitamin A, fermentation product |
| *Litchi* | Vitamin B1, B2, citric acid, fermentation product | Papaya | Vitamin B, C, E, citric acid, carotene, fermentation product |
| Balsam pear | Vitamin B1, B2, citric acid, fermentation product | Onion | Vitamin B, C, carotene, fermentation product |
| Leek | Vitamin B1, B2, citric acid, fermentation product | Mulberry | Vitamin B1, B2, citric acid, fermentation product |
| Pomegranate | Vitamin B1, B2, citric acid, fermentation product | Sugar beet | Betaine, fermentation product |
| Pitaya | Vitamin B1, B2, citric acid, fermentation product | Lemon | citric acid, fermentation product |

II. Fermenting the Fruits and the Vegetables
1. Selecting and Buying Strains

Probiotic strains are bought from micro-biology institute of Chinese Sciences Academy, the probiotics are *Lactobacillus acidophilus* CGMCC 1.1854, *Bifidobactreium longum* CGMCC 1.2186, *Lactobacillus delbrueckii* subsp. *bulgaricus* CGMCC 1.1480, and *Streptococcus thermophilus* CGMCC 1.2471. All of the strains are preserved in sand tube, and are used as original strains.

2. Preparing Master Seeds

Preparing master seeds of the probiotics (Generations of transfer of the mater seeds is not more than 10, and the generations in the present invention is 4.) comprises:

(1) taking 1/10 of the sand tube of *Lactobacillus acidophilus* CGMCC 1.1854, *Bifidobactreium longum* CGMCC 1.2186, *Lactobacillus delbrueckii* subsp. *bulgaricus* CGMCC 1.1480, and *Streptococcus thermophilus* CGMCC 1.2471 with a sterile stainless steel spoon, wherein rest of the probiotics is cryopreserved, respectively inoculating the probiotics in 50 ml of MRS liquid medium (250 triangular flask) (10 g/l peptone, 10 g/l beef extract, 5 g/l yeast extract, 20 g/l glucose, 1 g/l tween-80, 2 g/l $K_2HPO_4$, 1 g/l tween-80, 5 g/l NaAC, 2 g/l ammonium citrate tribasic, 0.2 g/l $MgSO_4$, 0.05 g/l $MnSO_4$, sterilization in a temperature of 121° C. for 20 min), and culturing the probiotics on a shaking table in a speed of 100 r/min and a temperature of 37° C. for 16 h;

(2) respectively taking one loop of each probiotics with a inoculating loop, respectively streak inoculating the probiotics in MRS solid medium (10 g/l peptone, 10 g/l beef extract, 5 g/l yeast extract, 20 g/l glucose, 1 g/l tween-80, 2 g/l $K_2HPO_4$, 1 g/l tween-80, 5 g/l NaAC, 2 g/l ammonium citrate tribasic, 0.2 g/l $MgSO_4$, 0.05 g/l $MnSO_4$, 1.5% agar, sterilization in a temperature of 121° C. for 20 min), culturing the probiotics in a incubator in a temperature of 37° C. for 16 h;

(3) respectively taking a bacterial colony which is most eugenic in each probiotics, respectively inoculating the bacterial colony in 50 ml of the MRS liquid medium, and culturing the bacterial colony on a shaking table in a speed of 100 r/min and a temperature of 37° C. for 16 h;

(4) respectively inoculating the bacterial colony in 500 ml of the MRS liquid medium, culturing the bacterial colony on the shaking table in a speed of 100 r/min and a temperature of 37° C. for 16 h, adding glycerol to a concentration of 20%, shaking up, storing the probiotics by 1 ml into freezing tubes, which are used as the master seeds of *Lactobacillus acidophilus*, *Bifidobactreium longum*, *Bifidobacterium breve*, and *Streptococcus thermophilus*, preserving in a temperature of −40° C.

3. Preparing Working Seeds

Preparing working seeds of the probiotics comprises steps of: (The transfer generations of working seeds is not more than 5, and the transfer generations in the present invention is 4.)

(1) respectively taking the master seeds of *Lactobacillus acidophilus* CGMCC 1.1854, *Bifidobactreium longum* CGMCC 1.2186, *Lactobacillus delbrueckii* subsp. *bulgaricus* CGMCC 1.1480, and *Streptococcus thermophilus* CGMCC 1.2471 with the sterile inoculating loop, respectively streak inoculating the master seeds on the MRS solid medium, and culturing the master seeds in the incubator in a temperature of 37° C. for 16 h;

(2) respectively taking a bacterial colony which is most eugenic in each probiotics, respectively inoculating the bacterial colony in 50 ml of the MRS liquid medium, and culturing the bacterial colony on the shaking table in a speed of 100 r/min and a temperature of 37° C. for 16 h;

(3) respectively inoculating the bacterial colony in 500 ml of the MRS liquid medium, and culturing the bacterial colony on the shaking table in a speed of 100 r/min and a temperature of 37° C. for 16 h; and (4) respectively inoculating the bacterial colony in 5000 ml of the MRS liquid medium, and culturing the bacterial colony on the shaking table in a speed of 100 r/min and a temperature of 37° C. for 16 h to obtain bacteria liquid of *Lactobacillus acidophilus* CGMCC 1.1854, bacteria liquid of *Bifidobactreium longum* CGMCC 1.2186, bacteria liquid of *Lactobacillus delbrueckii* subsp. *bulgaricus* CGMCC 1.1480, and bacteria liquid of *Streptococcus thermophilus* CGMCC 1.2471, wherein above bacteria liquids are all whole fermenting products in the fermenting container.

4. Fermenting the Fruits and the Vegetables

Fermenting the fruits and the vegetables comprises steps of:

1) weighing the materials in above Table 1, and taking 15 kg of every kind;
2) washing the materials, drying, and weighing;
3) smashing the materials into pieces of 40~50 meshes, adding the materials into a fermenter,
   wherein practical feeding amount is 2400 kg for a fermenter of 3t (Weight of effective solvents=3t*0.8=2.4t.), and a proportion of the fruits and vegetables and water is 1:1, e.g., the weight of the fruits and vegetables is 1200 kg, and the weight of the water is 1200 kg;
4) adding 5000 ml of each of the bacteria liquid of *Lactobacillus acidophilus* CGMCC 1.1854, the bacteria liquid of *Bifidobactreium longum* CGMCC 1.2186, the bacteria liquid of *Lactobacillus delbrueckii* subsp. *bulgaricus* CGMCC 1.1480, and the bacteria liquid of *Streptococcus thermophilus* CGMCC 1.2471 into the fermenter, controlling the fermenting temperature being 23° C., stirring for 15 d;
5) filtering the fermenting product with a filter cloth of 200 meshes, and removing residues of the fruits and vegetables to obtain filtrate; and
6) ultrafiltering the filtrate in a molecular weight of 100,000 (a liquid inlet pressure is 1.3 kg, and a liquid outlet pressure is 0.5 kg) to obtain 1200~1500 kg of clear liquid, sealing the clear liquid, preserving the clear liquid in a temperature of 4° C. to obtain the fermentation broth of fruits and vegetables.

III. Detecting

The fermentation broth of fruits and vegetables mainly comprises: lactic acid and acetic acid, so acidity is identified as characteristic components of the fermentation broth of fruits and vegetables, which is preferably embodied as followed.

The acidity of the fermentation broth of fruits and vegetables refers to ml number/volume of NaOH solution of 0.1N consumed to titrate 100 ml of the fermentation broth of fruits and vegetables, and 10 ml of sample of the fermentation broth of fruits and vegetables is usually used when detecting.

Detecting comprises steps of: taking 10 ml of the fermentation broth of fruits and vegetables, 20 ml of water, and 0.5 ml of phenolphthalein indicator, processing titration with NaOH standard solution of 0.1N until mixture turns to reddish without fading in a period of 30 seconds. Calculating formula: Acidity=volume of the NaOH standard solution of 0.1N consumed*10

Result: The acidity of the product is 42.

Method 2

I. Fruits and Vegetables Selected are Same as Method 1.

II. Fermenting the Fruits and the Vegetables

Extracting method is mainly same as method 1, except that 2000 ml of each of the bacteria liquid of *Lactobacillus acidophilus* CGMCC 1.1854, the bacteria liquid of *Bifido-* bactreium longum CGMCC 1.2186, the bacteria liquid of Lactobacillus delbrueckii subsp. bulgaricus CGMCC 1.1480, and the bacteria liquid of Streptococcus thermophilus CGMCC 1.2471 are added, the weight of the fruits and vegetables added is 1000 kg, and the weight of the water is 1000 kg.

Fermenting temperature of the fermentation broth of fruits and vegetables is 18° C., and fermenting period is 10 d.

In the preparations of the bacteria liquid of Lactobacillus acidophilus, the bacteria liquid of Bifidobactreium longum, the bacteria liquid of Lactobacillus delbrueckii subsp. bulgaricus, and the bacteria liquid of Streptococcus thermophilus, fermenting temperatures are all 20° C., and fermenting periods are all 15 h.

III. Detecting

Detecting method is same as method 1, and there is no marked difference in the result and the steps.

Method 3

I. Fruits and Vegetables Selected are Same as Method 1.
II. Fermenting the Fruits and the Vegetables Extracting method is mainly same as method 1, except that 8000 ml of each of the bacteria liquid of Lactobacillus acidophilus CGMCC 1.1854, the bacteria liquid of Bifidobactreium longum CGMCC 1.2186, the bacteria liquid of Lactobacillus delbrueckii subsp. bulgaricus CGMCC 1.1480, and the bacteria liquid of Streptococcus thermophilus CGMCC 1.2471 are added, the weight of the fruits and vegetables added is 1500 kg, and the weight of the water is 1500 kg.

Fermenting temperature of the fermentation broth of fruits and vegetables is 37° C., and fermenting period is 180 d.

In the preparations of the bacteria liquid of Lactobacillus acidophilus, the bacteria liquid of Bifidobactreium longum, the bacteria liquid of Lactobacillus delbrueckii subsp. bulgaricus, and the bacteria liquid of Streptococcus thermophilus, fermenting temperatures are all 41° C., and fermenting periods are all 36 h.

III. Detecting

Detecting method is same as method 1, and there is no marked difference in the result and the steps.

Example 2

Experimental Research on a Function of Improving Immunity of the Fermentation Broth of Fruits and Vegetables 1. Materials and Methods
1.1. Test Substances The fermentation broth of fruits and vegetables obtained according to the embodiment 1 has a mass density of 1.01. Solutions of various dose or concentration are prepared by adding distilled water.

1.2. Experimental Animal 200 healthy female mice of Kunming species are provided by experimental animal center of Jilin University, which weigh 18~22 g. Feed and bedding are also provided by the experimental animal center of Jilin University.

1.3. Environment of Animal Room

Temperature 20° C.~22° C., humidity 45%~50%

1.4. Choosing Dosage 200 female mice are divided into 5 parts. 40 mice in the each part are randomly divided into 4 groups, i.e., a control group and three dosage groups, and each group comprises 10 mice, wherein the control group is processed with intragastric administration by feeding equivalent volume of distilled water. Experimental dosages of the other three dosage groups are designed as 10 ml/kg, 6.6 ml/kg and 3.3 ml/kg.

1.5. Experimental Method

The three dosage groups are processed with intragastric administration one time every day according to the experimental dosages, and the control group is processed with intragastric administration by feeding equivalent volume of distilled water. Volumes of intragastric administration are all 0.2 ml/10 g. Various immunity indexes are respectively determined after 30 days. The experimental methods are as follows.

1.5.1. Determination of Delayed-Type Hypersensitivity (DTH) of Mice

On $26^{th}$ day of intragastric administration, 0.2 ml of sheep red blood cell (SRBC, Beijing Dingguo Biological technology Co. Ltd., v/v) having a concentration of 2% is injected into abdominal cavities of the mice to cause sensitization. On $4^{th}$ day after being immune, SRBC of a concentration of 20% (20 μl/mice) is injected into left rear vola pedis of each mouse to attack. A thickness at a same position on the left rear vola pedis of each mouse is measured 24 h before and after attacking. Difference between the thickness before attacking and the thickness after the attacking is calculated. Results of the dosage groups and the control group are compared and processed with analysis of variance. Results are shown in Table 1.

TABLE 1

Determination results of DTH of mice fed with fermentation broth of fruits and vegetables

| Group (ml/kg) | Animal amount | Thickness Difference of vola pedis (mm) |
| --- | --- | --- |
| 10 | 10 | 0.839 ± 0.352** |
| 6.6 | 10 | 0.854 ± 0.361** |
| 3.3 | 10 | 0.612 ± 0.102 |
| Control | 10 | 0.571 ± 0.044 |

Compared to the control group,
*$p < 0.05$, and
**$p < 0.01$.

It is shown in the table 1, after the mice are process with intragastric administration by feeding fermentation broth of fruits and vegetables of different dosages for 30 days, compared to the control group, swelling of the vola pedis of the mice in the group fed with higher dosage and middle dosage significantly increases ($p<0.01$), differences have remarkable statistical significance.

1.5.2. Experiment of Transformation of Splenic Lymphocyte of Mice Induced by ConA (MTT Method)

On $26^{th}$ of intragastric administration, spleens of the mice in the four groups are taken out sterilely to prepare suspension of spleen cells, and a concentration of the spleen cells is adjusted to $3\times10^6$/ml by using RPMI1640 complete medium (brought from Beijing Dingguo Biological technology Co. Ltd). Mixed lymphocyte reactions are processed according to procedures of the MTT method, and absorbances (A) of the suspension are measured at a wavelength of 570 nm. Absorbance differences between $ConA^+$ and $ConA^-$ are calculated. Results of the dosage groups and the control group are compared and processed with analysis of variance. Results are shown in Table 2.

TABLE 2

Determination results of transformation of splenic lymphocyte of mice fed with fermentation broth of fruits and vegetables

| Group (ml/kg) | Animal amount | Difference between ConA$^+$ and ConA$^-$ |
|---|---|---|
| 10 | 10 | 0.132 ± 0.085** |
| 6.6 | 10 | 0.121 ± 0.072** |
| 3.3 | 10 | 0.105 ± 0.066 |
| Control | 10 | 0.101 ± 0.021 |

Compared to the control group,
*p < 0.05, and
**p < 0.01.

It is shown in the table 2, compared to the control group, transformation rate of splenic lymphocyte induced by ConA of the mice in the group fed with higher dosage and middle dosage significantly increases (p<0.01), differences have remarkable statistical significance.

1.5.3. Determination of Serum Hemolysin

On 25$^{th}$ of intragastric administration, 0.2 ml of SRBC having a concentration of 20% is injected into abdominal cavity of each mouse. On 5$^{th}$ day after being immune, eyeball enucleation is processed to take blood. Serum is separated, and serum hemolysin is determined on a microscale blood clot plate. The serum is incubated in a temperature of 37° C. for 3 hours, and aggregation degrees of blood cells are collected, and corresponding antibody titre levels are calculated. Results of the dosage groups and the control group are compared and processed with analysis of variance. Results are shown in Table 3.

TABLE 3

Determination results of serum hemolysin of mice fed with fermentation broth of fruits and vegetables

| Group (ml/kg) | Animal amount | antibody titre levels |
|---|---|---|
| 10 | 10 | 177.05 ± 16.54** |
| 6.6 | 10 | 165.25 ± 14.69** |
| 3.3 | 10 | 176.67 ± 16.73** |
| Control | 10 | 149.35 ± 7.88 |

Compared to the control group,
*p < 0.05, and
**p < 0.01.

It is shown in the table 1, compared to the control group, antibody titre levels of mice in the dosage groups are all higher than that of the mice in the control group (p<0.01), differences have remarkable statistical significance.

1.5.4. Determination of Plaque Forming Cells (PFC)

On 25$^{th}$ of intragastric administration, 0.2 ml of having a concentration of 20% is injected into abdominal cavity of each mouse. On 5$^{th}$ day after being immune, the mice are executed, and dissected to take spleens to prepare suspension of spleen cells. A concentration of the spleen cells is adjusted to 5×10$^6$/ml by using RPMI1640 complete medium. Agarose slides are prepared according to procedures. Complement is added after agarose slides are incubated in a CO$_2$ incubator (37° C., 5% CO$_2$) for 1.5 h, and then the agarose slides are incubated again for 1.5 h. Amount of haemolysis plaque formed on each agarose slide is counted. Results of the dosage groups and the control group are compared and processed with analysis of variance. Results are shown in Table 4.

TABLE 4

Determination results of plaque forming cells of mice fed with fermentation broth of fruits and vegetables

| Group (ml/kg) | Animal amount | Amount of haemolysis plaque formed/ 10$^6$ spleen cells |
|---|---|---|
| 10 | 10 | 876 ± 308* |
| 6.6 | 10 | 791 ± 135 |
| 3.3 | 10 | 776 ± 175 |
| Control | 10 | 605 ± 142 |

Compared to the control group,
*p < 0.05, and
**p < 0.01.

It is shown in the table 4, difference of the amounts of haemolysis plaque between the higher dosage group and the control group has statistical significance (p<0.05). Difference of the amounts of haemolysis plaque between the middle dosage group and the control group, and difference of the amounts of haemolysis plaque between the lower dosage group and the control group have no statistical significance (p>0.05).

1.5.5. Carbon Clearance Test of Mice

India ink (4 times diluted) of 0.1 ml/10 g is injected in caudal vein of the mice in the four groups in order. At 2 min and 10 min after injection of the ink, 20 µl of blood is respectively taken at inner canthus of each mouse on time. The blood is rapidly added into 2 ml of sodium carbonate solution having a concentration of 0.1%, and the solution is shaken up. Absorbances (A) of the solution are measured at a wavelength of 600 nm with an ultraviolet and visible spectrophotometer. Meanwhile, liver and spleen of each mouse are weighed, and phagocytic index are calculated according a formula. Results of the dosage groups and the control group are compared and processed with analysis of variance. Results are shown in Table 5.

TABLE 5

Determination results of carbon clearance test of mice fed with fermentation broth of fruits and vegetables

| Group (ml/kg) | Animal amount | Phagocytic index |
|---|---|---|
| 10 | 10 | 3.859 ± 0.305* |
| 6.6 | 10 | 3.687 ± 0.381 |
| 3.3 | 10 | 3.406 ± 0.318 |
| Control | 10 | 3.384 |

Compared to the control group,
*p < 0.05, and
**p < 0.01.

It is shown in the table 5, difference of carbon clearance phagocytic index between the higher dosage group and the control group has statistical significance (p<0.05). Difference of carbon clearance phagocytic index between the middle dosage group and the control group, and difference of carbon clearance phagocytic index between the lower dosage group and the control group have no statistical significance (p>0.05).

1.5.6. Experiment of Swallowing of Chicken Erythrocytes by Macrophages in Abdominal Cavities of Mice After last time of feeding the test substance, 1 ml of chicken erythrocytes suspension having a concentration of 20% is injected into abdominal cavity of each mouse. After 30 min, the mice are executed, and 2 ml of physiological saline is injected into abdominal cavity of each mouse. After each mouse is shaken for 1 min, washing liquid in the abdominal cavity is taken out, and slides are prepared. The slides are incubated in a temperature of 37° C. for 30 min After the slides are rinsed and fixed, the slides are dyed and examined with a microscope. An amount of macrophages swallowing chicken erythrocytes is counted, and an amount of chicken erythrocytes swallowed by macrophages is counted. Converted values of phagocytic rate and phagocytic indexes of the dosage groups and the control group are compared, and processed with analysis of variance. Results are shown in Table 6.

TABLE 6

Determination results of swallowing of chicken erythrocytes by macrophages of mice fed with fermentation broth of fruits and vegetables

| Group (ml/kg) | Animal amount | Macrophage amount | Converted value of phagocytic rate | Phagocytic index |
|---|---|---|---|---|
| 10 | 10 | 100 × 10 | 63.54 ± 4.98 | 2.79 ± 1.09* |
| 6.6 | 10 | 100 × 10 | 62.18 ± 3.85 | 2.64 ± 1.02* |
| 3.3 | 10 | 100 × 10 | 60.63 ± 2.82 | 2.25 ± 0.78 |
| Control | 10 | 100 × 10 | 48.21 ± 2.05 | 1.54 ± 1.05 |

Compared to the control group,
*$p < 0.05$, and
**$p < 0.01$.

It is shown in the table 6, converted value of phagocytic rate of swallowing of chicken erythrocytes by macrophages of mice in the dosage groups are higher than that in the control group. Difference between higher dosage group and the control group has statistical significance ($p<0.05$). Difference between the middle dosage group and the control group has statistical significance ($p<0.05$). Difference between the lower dosage group and the control group has statistical significance ($p>0.05$).

It is proved by animal experiments that the fermentation broth of fruits and vegetables has positive effects on cellular immune function, humoral immune function and mononuclear macrophage function of mice. It is preliminarily proved that the fermentation broth of fruits and vegetables can improve immunity.

The compositions obtained according to the method 2 and method 3 in the embodiment 1 are detected by methods same as above, and there is no significant difference between results of the compositions obtained according to the method 2 and method 3, and the results of the composition obtained according to the method 1.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for preparing a fermentation broth of fruits and vegetables comprising the steps of:
  (i) mixing a sufficient quantity of fruits and vegetables with a *Lactobacillus acidophilus* culture broth, a *Bifidobacterium longum* culture broth, a *Lactobacillus delbrueckii* subsp. *bulgaricus* culture broth, and a *Streptococcus thermophilus* culture broth to obtain a mixture, and
  (ii) fermenting the mixture for a suitable time to obtain said fermentation broth.

2. The method according to claim 1, further comprising smashing the fruits and vegetables into pieces having a diameter at a range of 40-50 meshes before step (ii); filtering the fermentation broth after step (ii); collecting the filtrate, and ultra-filtrating said filtrate.

3. The method according to claim 1, wherein the fruits and vegetables are a mixture of 54 kinds of fruits and vegetables, which are konjak, eggplant, asparagus, spinach, bean sprout, broccoli, cabbage, radish, cucumber, peas, red pepper, celery, scallion, garlic, grapes, grapefruit, watermelon, peach, tangerine, blue berry, sweet orange, banana, litchi, balsam pear, leek, pomegranate, pitaya, carrot, tomato, Chinese cabbage, parsley, bell pepper, lettuce, pear, ginger, taro, kidney bean, pumpkin, lotus root, cherry, kiwi fruit, plum, strawberry, fig, kumquat, mandarin orange, Nanguo pear, cantaloupe, Hami melon, papaya, onion, mulberry, sugar beet, and lemon.

4. The method according to claim 1 wherein the mass of each fruit or vegetable is equal with each other.

5. The method according to claim 1, wherein the mixture further comprises water, and wherein the proportion of the fruits and vegetables, *Lactobacillus acidophilus* culture broth, *Bifidobacterium longum* culture broth, *Lactobacillus delbrueckii* subsp. *bulgaricus* culture broth, *Streptococcus thermophilus* culture broth, and water in said mixture is 1000-1500 kg:2000-8000 ml:2000-8000 ml:2000-8000 ml:2000-8000 ml:1000-1500 kg, respectively.

6. The method according to claim 5, wherein the mixture further comprises water, and wherein the proportion of the fruits and vegetables, *Lactobacillus acidophilus* culture broth, *Bifidobacterium longum* culture broth, *Lactobacillus delbrueckii* subsp. *bulgaricus* culture broth, *Streptococcus thermophilus* culture broth, and water in said mixture is 1000 kg, 1200 kg, or 1500 kg:2000 ml, 5000 ml, or 8000 ml:2000 ml, 5000 ml, or 8000 ml:2000 ml, 5000 ml, or 8000 ml:2000 ml, 5000 ml, or 8000 ml: 1000 kg, 1200 kg, or 1500 kg, respectively.

7. The method according to claim 1, wherein the culture broths of *Lactobacillus acidophilus*, *Bifidobacterium longum*, *Lactobacillus delbrueckii* subsp. *bulgaricus*, and *Streptococcus thermophilus* are prepared by a method comprising steps of: cultivating each strain separately in MRS liquid medium at a temperature of 20-41° C. for a period of 15-36 hours to obtain said culture broths.

8. The method according to claim 7, wherein each of the culture broths are cultured at a temperature of 20° C., 37° C., or 41° C., for a period of 15 hours, 16 hours, or 36 hours.

9. The method according to claim 1, wherein the *Lactobacillus acidophilus* is *Lactobacillus acidophilus* CGMCC 1.1854, the *Bifidobacterium longum* is *Bifidobacterium longum* CGMCC 1.2186, the *Lactobacillus delbrueckii* subsp. *bulgaricus* is *Lactobacillus delbrueckii* subsp. *bulgaricus* CGMCC 1.1480, and the *Streptococcus thermophilus* is *Streptococcus thermophilus* CGMCC 1.2471.

10. The method according to claim 1, wherein the fermenting is conducted at a temperature of 18-37° C. for a period of 10-180 days.

11. The method according to claim 10, wherein the fermentation temperature is 18° C., 23° C., or 37° C., and the fermenting period is 10 days, 15 days, or 180 days.

12. The method according to claim 10, further comprising smashing the fruits and vegetables into pieces having a diameter at a range of 40-50 meshes before the step (i); filtering a fermentation broth after the step (ii); collecting the filtrate, and ultra-filtrating said filtrate.

13. The method according to claim 12, wherein the fruits and vegetables are a mixture of 54 kinds of fruits and vegetables, which are konjak, eggplant, asparagus, spinach, bean sprout, broccoli, cabbage, radish, cucumber, peas, red pepper, celery, scallion, garlic, grapes, grapefruit, watermelon, peach, tangerine, blue berry, sweet orange, banana, litchi, balsam pear, leek, pomegranate, pitaya, carrot, tomato, Chinese cabbage, parsley, bell pepper, lettuce, pear, ginger, taro, kidney bean, pumpkin, lotus root, cherry, kiwi fruit, plum, strawberry, fig, kumquat, mandarin orange, Nanguo pear, cantaloupe, Hami melon, papaya, onion, mulberry, sugar beet, and lemon.

14. The method according to claim 13 wherein the mass of each fruit or vegetable is equal with each other.

15. The method according to claim 14, wherein the mixture further comprises water, and wherein the proportion of the fruits and vegetables, *Lactobacillus acidophilus* culture broth, *Bifidobacterium longum* culture broth, *Lactobacillus delbrueckii* subsp. *bulgaricus* culture broth, *Streptococcus thermophilus* culture broth, and water in said mixture is 1000-1500 kg:1000-1500 kg:2000-8000 ml:2000-8000 ml:2000-8000 ml:2000-8000 ml, respectively.

16. The method according to claim 15, wherein the culture broths of *Lactobacillus acidophilus*, *Bifidobacterium longum*, *Lactobacillus delbrueckii* subsp. *bulgaricus*, and *Streptococcus thermophilus* are prepared by a method comprising steps of: cultivating each strain separately in MRS liquid medium at a temperature of 20-41° C. for a period of 15-36 hours to obtain said culture broths.

17. The method according to claim 16, wherein the *Lactobacillus acidophilus* is *Lactobacillus acidophilus* CGMCC 1.1854, the *Bifidobacterium longum* is *Bifidobacterium longum* CGMCC 1.2186, the *Lactobacillus delbrueckii* subsp. *bulgaricus* is *Lactobacillus delbrueckii* subsp. *bulgaricus* CGMCC 1.1480, and the *Streptococcus thermophilus* is *Streptococcus thermophilus* CGMCC 1.2471.

* * * * *